United States Patent [19]

Barnard et al.

[11] Patent Number: 5,811,564

[45] Date of Patent: Sep. 22, 1998

[54] POLYCARBOSILANE HYDROXIDES AND METHODS FOR THEIR PREPARATION

[75] Inventors: Thomas Duncan Barnard, Midland, Mich.; Gregg Alan Zank, Tokyo, Japan

[73] Assignee: Dow Corning Corporation, Midland, Mich.

[21] Appl. No.: 992,249

[22] Filed: Dec. 17, 1997

[51] Int. Cl.$^6$ ........................................... C07F 7/08
[52] U.S. Cl. ........................ 556/435; 556/431; 528/25; 528/28; 528/31
[58] Field of Search .................................. 556/435, 431; 528/25, 28, 31

[56] References Cited

U.S. PATENT DOCUMENTS

| | | | |
|---|---|---|---|
| 4,052,430 | 10/1977 | Yajima et al. | 260/448.2 |
| 4,100,233 | 7/1978 | Yajima et al. | 423/345 |
| 4,220,600 | 9/1980 | Yajima et al. | 556/434 |
| 4,248,814 | 2/1981 | Yajima et al. | 264/63 |
| 4,283,376 | 8/1981 | Yajima et al. | 423/345 |
| 5,677,410 | 10/1997 | Mager et al. | 556/440 UX |

OTHER PUBLICATIONS

Synthesis of continuous silicon carbide fibre with high tensile strenght and high Young's modulus; Journal of Materials Science; vol. 13; 1978; pp. 2569–2576.

Synthesis of continuous silicon carbide fibre; Journal of Materials Science; vol. 15; 1980; pp. 720–728.

*Primary Examiner*—Paul F. Shaver
*Attorney, Agent, or Firm*—Sharon K. Severance

[57] ABSTRACT

This invention pertains to polycarbosilane hydroxides which contain units of the formula

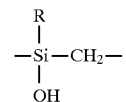

where R is a hydrocarbon having from 1 to 20 carbon atoms and to methods for their manufacture. The polycarbosilane hydroxides may be prepared by the oxidation of a polycarbosilane.

17 Claims, No Drawings

POLYCARBOSILANE HYDROXIDES AND METHODS FOR THEIR PREPARATION

BACKGROUND OF THE INVENTION

This invention pertains to polycarbosilane hydroxides (PCS—OH) and methods for their preparation. The polycarbosilane hydroxides are prepared by the oxidation of polycarbosilanes. The resulting polymer is useful in applications where polycarbosilane typically is not useful such as binders for powders, matrices for ceramic matrix composites, precursors to fibers employing solution spinning and for conversion to fine ceramic powders by bulk pyrolysis.

Polycarbosilane is one of most well known polymeric precursors to ceramic materials. Polycarbosilanes generally contain units of the general formula ≡Si—$CH_2$— as well as Si—H functionality which may be in the form of =HSi—$CH_2$—.

The widest use for this polymer is as a precursor to ceramic fibers such as Nicalon® SiCO ceramic fibers. To produce ceramic fibers from polycarbosilanes, it is generally required to cure the polycarbosilane in oxygen at a temperature of about 170° C. or more to render the fiber infusible prior to pyrolysis. This cure mechanism may be set forth as:

2≡SiH+$O_2$→≡Si—O—Si+$H_2O$

It has now been found that by using the proper reaction conditions that a polycarbosilane hydroxide (PCS—OH) may be isolated. It is therefore an object of this invention to provide polycarbosilane hydroxides.

It is further an object of this invention to provide method for making polycarbosilane hydroxides.

SUMMARY OF THE INVENTION

This invention pertains to polycarbosilane hydroxides and to methods for their manufacture. The polycarbosilane hydroxides of this invention contain units of the formula

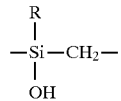

where R is a hydrocarbon having from 1 to 20 carbon atoms. The polycarbosilane hydroxides may be prepared by the oxidation of a polycarbosilane. In particular, the polycarbosilane hydroxide may be prepared by heating a polycarbosilane at a temperature of 60° C. to 110° C. in an environment containing oxygen. Additionally, the polycarbosilane hydroxide may be prepared by heating a polycarbosilane dissolved in a non-flammable solvent at a temperature of above 90° C. while sparging the solvent solution with an environment containing oxygen for a period of time sufficient to form the polycarbosilane hydroxide. Finally the polycarbosilane hydroxide may be prepared by employing an organic oxidizer such as $Me_3NO$.

The Invention

The polycarbosilanes produced herein contain units of the general formula

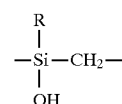

where R is a hydrocarbon having from 1 to 20 carbon atoms. The hydrocarbons include alkyl radicals such as methyl, ethyl, propyl, and others; aryl radicals such as pheny and unsaturated hydrocarbon radicals such as vinyl. R is preferably methyl.

In addition, the above hydrocarbon radicals can contain hetero atoms such as silicon, nitrogen, and boron. The polycarbosilane hydroxides may additionally contain units of the formulas $(R^1Si(CH_2)_{3/2})$, $(R^1{}_2SiCH_2)$ and $(R^1{}_3Si(CH_2)_{1/2})$ where each $R^1$ is independently selected from the group consisting of hydrogen, hydroxyl and R. The polycarbosilane hydroxide produced herein typically contain from 1 to 25 weight percent hydroxyl functionality, preferably 5 to 15 weight percent.

The polycarbosilane hydroxides are produced by oxidizing polycarbosilanes having —SiH functionality. These —SiH containing polycarbosilanes are known in the art and usually contain units of the type ($RHSiCH_2$), where each R is a hydrocarbon having 1 to 20 carbon atoms. These polycarbosilanes typically contain at least 0.1 weight percent silicon bonded hydrogen, preferably 0.2 to 2 weight percent silicon bonded hydrogen. Polycarbosilanes useful herein are described in U.S. Pat. No. 4,052,430 to Yajima et al. and U.S. Pat. No. 4,100,233 to Yajima et al., both of which are incorporated herein. Specifically, these patents teach a method for producing polycarbosilanes by heating and condensing polysilanes at a temperature of 300° C. to 2000° C. in an inert gas, hydrogen, or vacuum. Other methods for producing polycarbosilanes are known in the art and may be used herein.

Preferred are polycarbosilanes containing repeating units of the formula

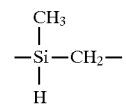

These polycarbosilanes are commercially available and may be purchased from Nippon Carbon Co.

The polycarbosilanes may also be substituted with various metal groups such as boron, aluminum, chromium, and titanium. The method used to prepare such polymers is not critical. Methods for preparation of metal substituted polycarbosilanes is described in U.S. Pat. No. 4,248,814 to Yajima et al., U.S. Pat. No. 4,283,376 to Yajima et al. and U.S. Pat. No. 4,220,600 to Yajima et al., all herein incorporated by reference.

The polycarbosilane hydroxide is produced by oxidation of the polycarbosilane. The oxidation of the polycarbosilane may be carried out by (I) heating a polycarbosilane at a temperature of 60° C. to 110° C. in an environment containing oxygen; (II) dissolving a polycarbosilane in a non-flammable solvent and thereafter heating the solvent solution of polycarbosilane at a temperature of 90° C. and above while sparging the solution with a gas containing oxygen or (III) by reacting the polycarbosilane with an organic oxidizer such as $Me_3NO$ to form the polycarbosilane hydroxide.

The first method for producing the polycarbosilane hydroxide comprises heating a polycarbosilane in an environment containing oxygen at a temperature of 60° C. to 110° C. Environments containing oxygen may be exemplified by air, oxygen, inert gases containing oxygen and others. Preferably the environment is air. The polycarbosilane is heated for a time sufficient to produce the polycarbosilane hydroxide. Typically the polycarbosilane is heated for a time sufficient to cause a 2% to 8% weight gain in the polycarbosilane. This weight gain indicates the conversion of the SiH functionality to SiOH functionality. Typically the polycarbosilane is heated for a period of 1 hour to 30 days. One skilled in the art would recognize that these conditions are at atmospheric pressure and that heating at pressures other than atmospheric may result in changes in the heating temperature and/or heating time.

Another method for producing the polycarbosilane hydroxide comprises dissolving the polycarbosilane in a non-flammable solvent and thereafter heating the solvent solution of a polycarbosilane at a temperature of 90° C. and above while sparging a gas containing oxygen through the solution. The solvent employed should be one in which the polycarbosilane is soluble and further is not flammable at the temperature to which it is heated. Solvents useful herein may be exemplified by, but not limited to, tetrachloroethylene, perchloroborzane, and others. The solvent solution is heated to a temperature of 90° C. or greater, preferably to a temperature of 100° C. to 150° C. A gas containing oxygen is sparged through the solution during the heating. Gases useful herein may be exemplified by, but not limited to air, oxygen, inert gases containing oxygen and others, preferably air. The flow of the gas should be sufficient to introduce sufficient oxygen into the solution to allow the conversion to proceed. One skilled in the art will be able to easily determine the appropriate flow rate.

The solution is heated and sparged with the oxygen containing gas for a time sufficient to allow the conversion of the polycarbosilane to polycarbosilane hydroxide. The time required to produce the polycarbosilane hydroxide will be dependent on the temperature to which the solution is heated, the amount of oxygen contained in the gas and the flow rate of the sparging. Typically, this will take from 1 hour to 24 hours. However, one skilled in the art will be able to monitor the extent of the reaction and determine the necessary time to complete the conversion. Further, one skilled in the art would recognize that these conditions are at atmospheric pressure and that heating at pressures other than atmospheric may result in changes in the heating temperature and/or heating time.

A third method for producing the polycarbosilane hydroxide comprises reacting a polycarbosilane with a organic oxidizer. Organic oxidizers useful herein are known in the art and may be exemplified by, but not limited to, Me$_3$NO, organic peroxides, and others; preferably Me$_3$NO. Typically this oxidation is carried out by dissolving the polycarbosilane in a solvent in which it is soluble. Suitable solvents may be exemplified by, but not limited to, toluene, xylene, petroleum ethers, and others; preferably toluene. The organic oxidizer is then added to the solvent solution of polycarbosilane and the solution is heated to reflux. The reaction is carried out for a time sufficient to convert the polycarbosilane to the polycarbosilane hydroxide. Typically this will be from 1 hour to 1 week, preferably from 12 to 36 hours. One skilled in the art would recognize that these conditions are at atmospheric pressure and that heating at pressures other than atmospheric may result in changes in the heating temperature and/or heating time.

The polycarbosilane hydroxides of the instant invention are useful in applications such as binders for powders, matrices for ceramic matrix composites, as precursors to fibers employing solution spinning and for conversion to fine ceramic powders by bulk pyrolysis without the need for extensive grinding.

Further, the polycarbosilane hydroxides may be further reacted to produce functionalized polycarbosilanes. In particular, the polycarbosilane hydroxide may be reacted with alkoxysilanes or alkylchlorosilanes to produce alkoxy functional polycarbosilanes or alkyl functional polycarbosilanes.

So that those skilled in the art can understand and appreciate the invention taught herein, the following examples are presented, it being understood that these examples should not be used to limit the scope of this invention found in the claims.

EXAMPLES

I. Materials

All organosiloxane materials were obtained from Dow Corning Corporation as intermediates or were purchased from Huls America. Polycarbosilane was obtained from Nippon Carbon Company.

Polymer pyrolysis was carried out in a Lindberg Model 54434 or similar tube furnace equipped with Eurotherm temperature controllers. In a typical pyrolysis a sample was weighed out (approx. 4 g) and placed in an alumina boat and then loaded into the furnace. The furnace was then purged with argon at a rate sufficient to achieve one turnover of the furnace atmosphere every 3 minutes. After purging 45 to 60 minutes the flow was reduced to allow for turnover every 6 minutes and the temperature raised to a final temperature and held 60 minutes. The ceramic sample was then weighed, and ground for testing and analysis.

II. Analysis

Solution NMR spectra were recorded on a Varian VXR 400S or Varian 200 MHz instrument.

Gel permeation chromatographic data were obtained on a Waters GPC equipped with a model 600E systems controller, model 410 differential refractometer detector interfaced to a Compaq 486/33 computer employing PE Nelson Turbochrom software; all values are relative to polystyrene standards.

Thermal gravimetric analysis were recorded on an Omnitherm TGA 951 analyzer interfaced to an IBM PS/2-50 Z computer with Thermal Sciences software.

Carbon, hydrogen and nitrogen analysis were done on a Perkin Elemer 2400 analyzer. Oxygen analysis was done on a Leco oxygen analyzer model RO-316 equipped with an oxygen denominator 316 (Model 783700) and an electrode furnace EF100. Silicon analysis was determined by a fusion technique which consisted of converting the solid to a soluble form and analyzing the solute for total silicon by Arl 3580 ICP-AES analysis.

The X-ray powder diffraction was carried out on a Siemens D5000 horizontal theta-theta automated goniometer, equipped with a sample spinner, low background sample holders, graphite monochromator, scintillation counter, long fine focus Cu tube, and computer controlled operation. The solid sample is always ground to a fine powder of −100 mesh and smaller without any grit feeling by using a boron carbide grinder to minimize the contamination from grinding. Scans are made at 1 degree 2 theta per minute from 6 to 80 2-theta with the x-ray tube operated at 40kV and 30 mA. The phase identification was quickly achieved by a computer search over a reference field of over 60,000.

Example 1

A powdered sample of polycarbosilane (40 g) was placed in a vacuum oven and the temperature ramped to 100° to 120° C. in air. The material was held there and periodically removed and weighed to monitor weight pick-up. After 21 days the material had picked up 5 to 7% of its weight and was removed. An IR spectra run on a sample showed both SiH and OH absorbences.

Example 2

220 g of polycarbosilane (Mn=741, Mw=3131) was dissolved in 2 Kg tetrachloroethylene in a 3-necked flask. The solution was heated to between 100° C. and 105° C. and oxygen gas sparged subsurface via a gas dispersion wand. After 12 h of reaction time, the heat was removed and a sample taken for IR spectrum. The IR showed the presence of OH and some SiH. The reaction was stopped and the solution was concentrated to 50 percent solids by removal of the solvent by rotary evaporation. The resulting solution had a Mn=793 and Mw=8891. The isolated polycarbosilane hydroxide solid had a Mn=1045 and Mw=31043.

The starting polycarbosilane and the resulting polymer were pyrolyzed according to the procedures described above. The results are below in Table 1.

TABLE 1

Ceramification Results of Polycarbosilane hydroxide produced in Example 2.

| Material | Ceramic Yield | % C | % Si |
|---|---|---|---|
| polycarbosilane | 62.0% | 36.0 | 60.5 |
| PCS—OH | 65.5% | 31.0 | 50.4 |

Example 3

20 g of polycarbosilane (Mn=720, Mw=2870) was dissolved in 130 g of toluene in a 3-necked flask fitted with an overhead stirrer and a water cooled condenser. To this was added 5.5 g of $Me_3NO$ and the resulting solution was heated to reflux for 48 hours. At that time the solution was cooled. An IR spectrum of the solution was taken which indicated the presence of OH and SiH. The product was isolated by filtration and removal of the solvent by rotary evaporation. The resulting material had a Mn=740 and Mw=3091.

What is claimed is:

1. A polycarbosilane hydroxide comprising units of the formula

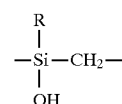

where R is a hydrocarbon having from 1 to 20 carbon atoms.

2. The polycarbosilane hydroxide as claimed in claim 1 where R is methyl.

3. The polycarbosilane hydroxide as claimed in claim 1 wherein there is additionally present at least one unit selected from the group consisting of the formulas $(R^1Si(CH_2)_{3/2})$, $(R^1{}_2Si(CH_2)_{2/2})$ and $(R^1{}_3Si(CH_2)_{1/2})$ where each $R^1$ is independently selected from the group consisting of hydrogen, hydroxyl and R.

4. The polycarbosilane hydroxide as claimed in claim 1 containing from 1 to 25 weight perce ydroxyl functionality.

5. A method for producing a polycarbosilane hydroxide wherein the method comprises oxidation of a polycarbosilane.

6. The method as claimed in claim 5 wherein the oxidation comprises heating the polycarbosilane at a temperature of 60° C. to 110° C. in an environment containing oxygen for a time sufficient to produce the polycarbosilane hydroxide.

7. The method as claimed in claim 6 wherein the environment containing oxygen is air.

8. The method as claimed in claim 6 wherein the polycarbosilane is heated for a period of 1 hour to 30 days.

9. The method as claimed in claim 5 wherein the oxidation comprises dissolving the polycarbosilane in a non-flammable solvent to form a solution and thereafter heating the solution of the polycarbosilane at a temperature of 90° C. or above while sparging the solution with a gas containing oxygen for a period of time sufficient to produce the polycarbosilane hydroxide.

10. The method as claimed in claim 9 wherein the solution is heated at a temperature of 100° C. to 150° C.

11. The method as claimed in claim 9 wherein the gas containing oxygen is air.

12. The method as claimed in claim 9 wherein the non-flammable solvent is tetrachloroethylene.

13. The method as claimed in claim 9 wherein the solution is heated for a period of 1 hour to 24 hours.

14. The method as claimed in claim 5 wherein the oxidation comprises treating the polycarbosilane with an organic oxidizer.

15. The method as claimed in claim 14 wherein the organic oxidizer is $Me_3NO$.

16. The method as claimed in 14 wherein the polycarbosilane is dissolved in a solvent and thereafter heated in the presence of the organic oxidizer for a time sufficient to produce the polycarbosilane hydroxide.

17. The method as claimed in claim 16 wherein the heating takes place for a time of from 1 hour to 1 week.

* * * * *